(12) United States Patent
Angelescu et al.

(10) Patent No.: US 9,322,812 B2
(45) Date of Patent: Apr. 26, 2016

(54) MULTIPLE SAMPLE CHROMATOGRAPHY USING A STOCHASTIC INJECTION TECHNIQUE

(71) Applicants: Institut Francais des Sciences et Technologies des Transports, De L'Amenagement et des Reseaux (IFSTTAR), Champ sur Marne (FR); Chambre de Commerce et D'Industrie de Region Paris Ile de France (ESIEE Paris), Noisy le Grand (FR)

(72) Inventors: Dan Angelescu, Le Perreux sur Marne (FR); William Cesar, Paris (FR); Tarik Bourouina, Joinville le Pont (FR)

(73) Assignees: Institut Francais des Sciences et Technologies des Transports, De L'Amenagement et des Reseaux (IFSTTAR) (FR); Chambre de Commerce et D'Industrie de Region Paris Ile de France (ESIEE Paris) (FR)

( * ) Notice: Subject to any disclaimer, the term of this patent is extended or adjusted under 35 U.S.C. 154(b) by 276 days.

(21) Appl. No.: 14/158,130

(22) Filed: Jan. 17, 2014

(65) Prior Publication Data

US 2015/0204825 A1     Jul. 23, 2015

(51) Int. Cl.
*G01N 30/16* (2006.01)
*G01N 30/86* (2006.01)

(52) U.S. Cl.
CPC ............... *G01N 30/16* (2013.01); *G01N 30/86* (2013.01)

(58) Field of Classification Search
CPC .......... G01N 2030/623; G01N 30/465; G01N 30/463; G01N 30/16; G01N 30/86; G01N 30/8658
USPC .................. 73/23.35, 23.36, 23.41
See application file for complete search history.

(56) References Cited

U.S. PATENT DOCUMENTS 4,006,350 A * 2/1977 Jokl .................. G01N 30/62
                                                   700/273
7,424,366 B2   9/2008 Angelescu et al.
(Continued)

FOREIGN PATENT DOCUMENTS

WO       2009108538 A2    9/2009

OTHER PUBLICATIONS

"Maximum-length Sequences EdT" (from the website : <http://www.commsp.ee.ic.ac.uk/~mrt102/projects/mls/MLS%20Theory.pdf>), published in 2005.
(Continued)

*Primary Examiner* — Freddie Kirkland, III
(74) *Attorney, Agent, or Firm* — Lerner, David, Littenberg, Krumholz & Mentlik, LLP

(57) ABSTRACT

The invention relates to a method for simultaneously analyzing at least two samples using a chromatography device comprising a chromatography column having an inlet and an outlet, and at least one detector placed at the outlet of the chromatography column, the method comprising steps of: injecting fractions of each independent sample at the inlet of the chromatography column, the fractions of each independent sample being injected according to a specific injection timing sequence derived from a pseudo-random binary sequence associated with said independent sample; recording a signal generated by said detector for a period of time at least equal to a duration of the longest of the specific injection timing sequences; cross-correlating the recorded signal and a derived correlation function, said derived correlation function being derived from the pseudo-random binary sequence associated with one of the independent samples, so as to obtain an individual correlogram signal specific to said independent sample; and analyzing data of interest of the individual correlogram signal so as to obtain an output signal indicative of a composition of the sample.

28 Claims, 13 Drawing Sheets

(56) References Cited

U.S. PATENT DOCUMENTS

| | | | | |
|---|---|---|---|---|
| 7,490,506 B2* | 2/2009 | Chaintreau | .......... | G01N 30/463 73/23.35 |
| 7,623,946 B2* | 11/2009 | Wang | .................. | G01N 30/463 422/89 |
| 8,297,135 B2 | 10/2012 | Trapp | | |
| 8,735,809 B2* | 5/2014 | Sumiyoshi | .............. | H01J 49/02 250/281 |

OTHER PUBLICATIONS

César et al. "High-sensitivity micro-gas chromatography using stochastic injection techniques", MEMS 2013, Poster.

César et al. "High-sensitivity micro-gas chromatography using stochastic injection techniques", pp. 997-1000, MEMS 2013, Taipei, Taiwan, Jan. 20-24, 2013.

Trap, Oliver, "Investigation of modulation parameters in multiplexing gas chromatography", Journal of Chromatography A, 1217 (2010) 6640-6645.

* cited by examiner

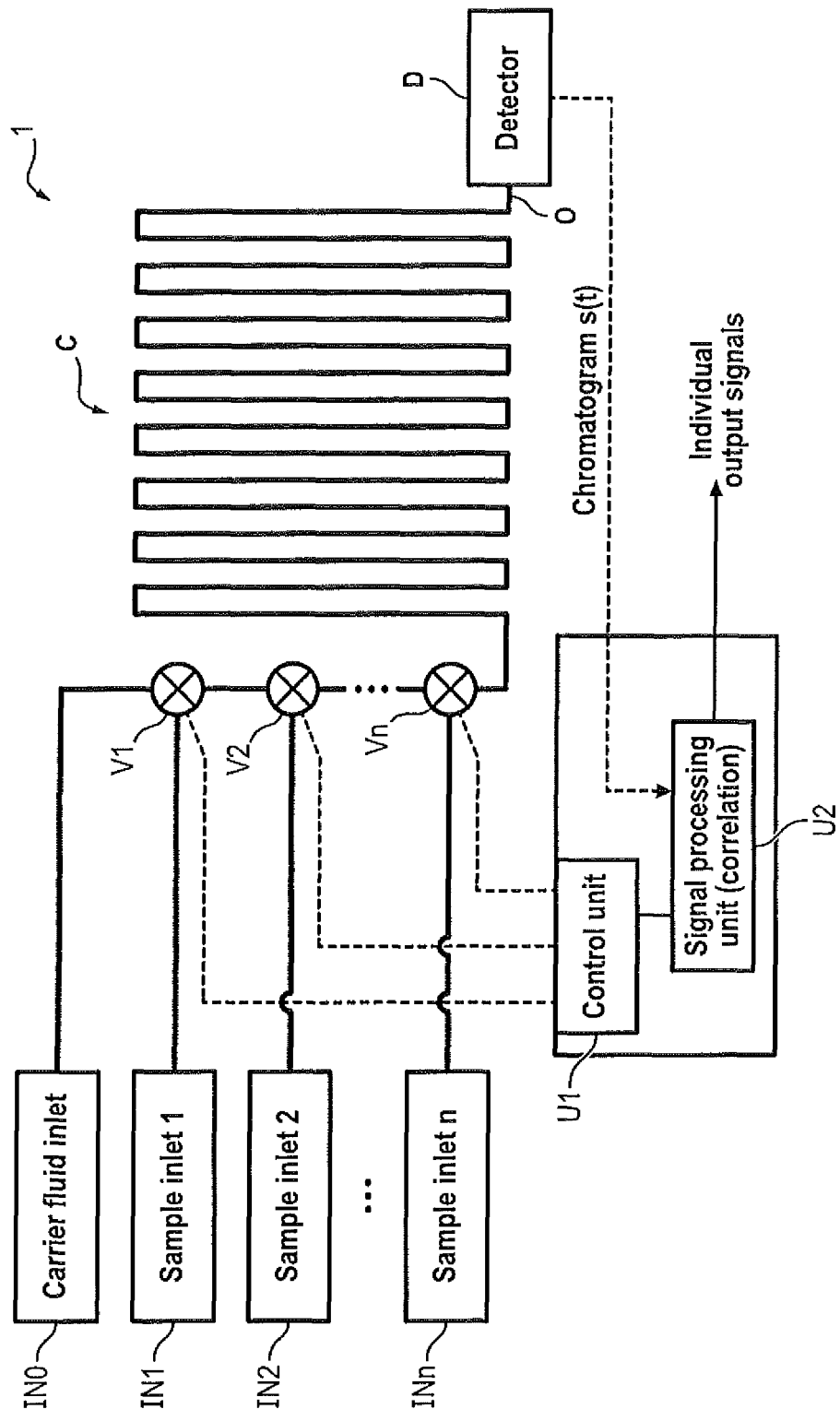

FIG. 2A
M-sequence: sequence of M elements in [-1,1]
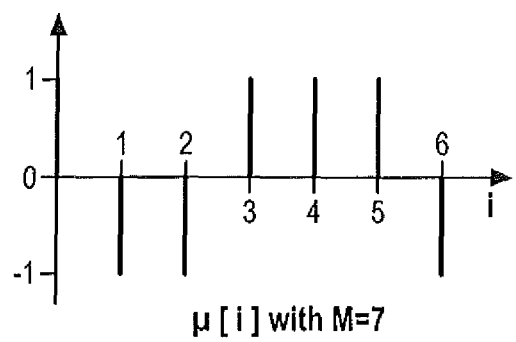
$\mu[\,i\,]$ with M=7
FIG. 2B
Injection timing function - continuous: $m[\,t\,]$
continuous variable is the time t
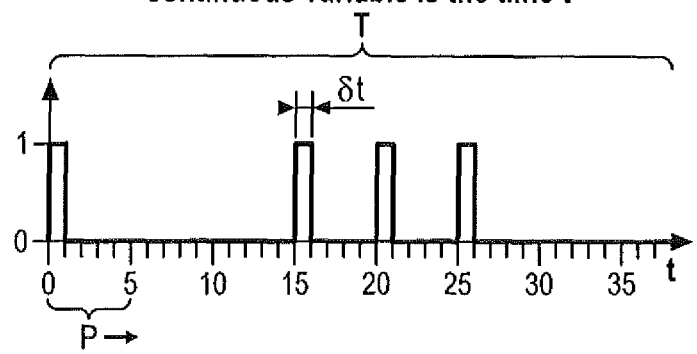
Injection timing function - discrete: $m[\,i\,]$
discrete variable is the index i, sampling period $\delta t$
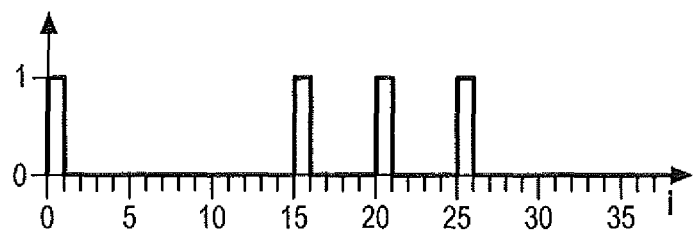

FIG. 2C
Derived correlation function - continuous: m' [ t ]
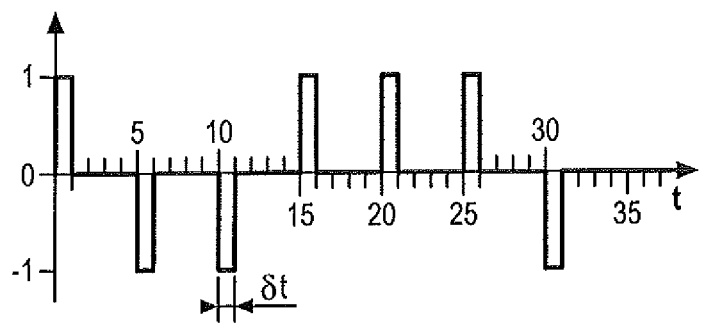
Derived correlation function - discrete: m' [ i ]
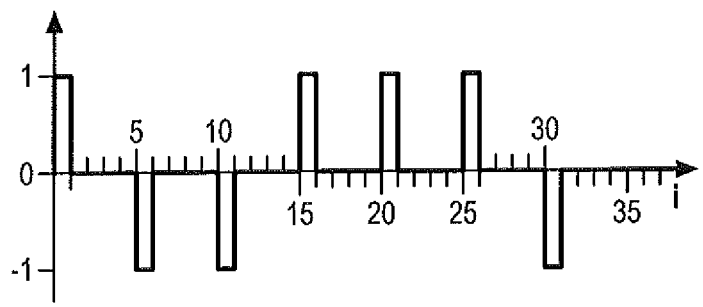

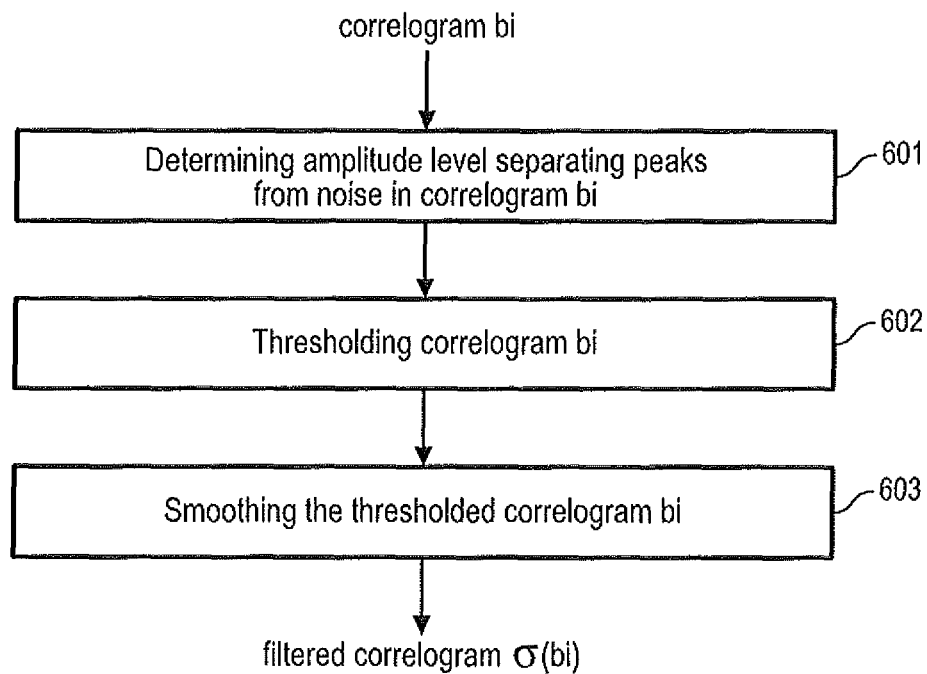
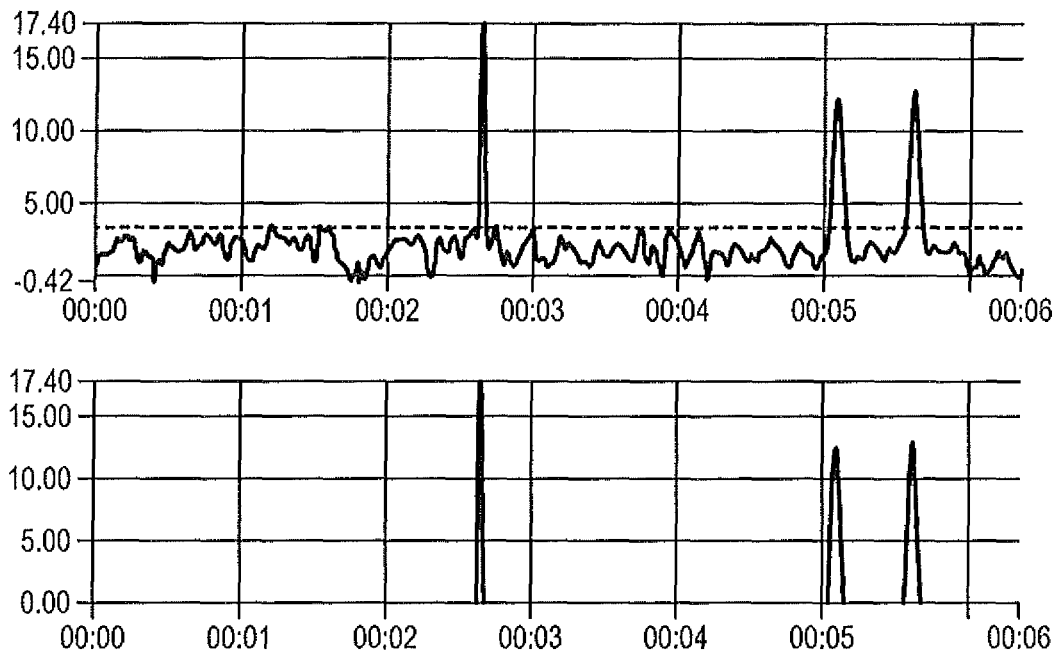

MULTIPLE SAMPLE CHROMATOGRAPHY USING A STOCHASTIC INJECTION TECHNIQUE

TECHNICAL FIELD

The invention relates to a method for simultaneously analyzing at least two samples using chromatography.

The invention deals more specifically with high sensitivity chromatography using stochastic injection techniques.

BACKGROUND OF THE INVENTION

Volatile organic compounds (VOCs) are major indoor and outdoor pollutants that can seriously affect human health and ecosystem. In order to ensure the safety of our environment, it is important to be able to measure and control the concentration of such gases with both high selectivity and sensitivity, and at multiple locations. Real-time monitoring of air pollution would be possible by processing data coming from multiple, fast and accurate sensors such as micro gas chromatographs (referred to as "GC" in the following).

Gas chromatography is one of the most popular analytical chemistry tools for the analysis of volatile compounds. This technique consists in detecting peaks corresponding to vapors that are separated upstream in a capillary column usually named chromatography column.

As common pollutants in air are often diluted to very low concentrations (sub-ppb), numerous efforts have been made to enhance the sensitivity of GC systems. This sensitivity is defined through the capability of the column to separate analytes, but also through the minimum concentration that can result in a detection peak that can be resolved from the detector noise. This limit of detection is a key performance parameter that many groups have tried to improve using different types of detectors, such as chemiresistors, micro thermal conductivity detectors or optical micro-interferometers. Another way to improve the sensitivity of a GC system is the use of a preconcentrator. This consists in amplifying the vapors concentration by collecting the analytes on an adsorbent medium during a certain period of time before quickly releasing them in the column, usually through a thermal desorption process. However, the use of this extra component has several drawbacks such as requiring extra power and space, and increasing the measurement time significantly.

Correlation chromatography is a set of techniques that consists in injecting samples according to a pseudo-random binary sequence and getting information from the resulting chromatogram thanks to signal processing. Such techniques have been recently investigated to improve the sensitivity of chromatography devices.

The U.S. Pat. No. 8,297,135 B2 (Trapp) describes a correlation chromatography technique for analyzing multiple samples simultaneously using a unique pseudo-random binary sequence. In this method, analysis is carried out by means of temporal multiplexing: the multiple samples to be analyzed are alternatively injected in "blocks" into a single column thanks to a single injector. A detector placed at an output of the column then acquires the combined signal and after signal processing produces several chromatograms, each chromatogram corresponding to a block of samples.

However a major drawback of the method described in U.S. Pat. No. 8,297,135 B2 is that one sample is injected at a time.

Therefore, the total time required for analyzing the multiple samples increases with the number of samples to be injected.

Besides, such technique produces chromatograms having poor signal-to-noise ratios which lead to inaccurate analysis of the corresponding samples.

SUMMARY OF THE INVENTION

In view of this prior art, an object of the invention is to reduce the amount of time required for analyzing multiple samples using chromatography.

Another object of the invention is to improve the accuracy of the data of interest that can be produced using a chromatography system.

According to a first aspect, the invention relates to a method for simultaneously analyzing at least two samples using a chromatography device comprising a chromatography column having an inlet and an outlet, and at least one detector placed at the outlet of the chromatography column, the method comprising steps of:
  injecting fractions of each independent sample at the inlet of the chromatography column, the fractions of each independent sample being injected according to a specific injection timing sequence derived from a pseudo-random binary sequence associated with said independent sample;
  recording a signal generated by said detector for a period of time at least equal to a duration of the longest of the specific injection timing sequences;
  cross-correlating the recorded signal and a derived correlation function, said derived correlation function being derived from the pseudo-random binary sequence associated with one of the independent samples, so as to obtain an individual correlogram signal specific to said independent sample; and
  analyzing data of interest of the individual correlogram signal so as to obtain an output signal indicative of a composition of the sample.

When using the method, multiple fractions of different samples are injected within the same period of time. A correlogram produced by the cross-correlation contains correlation noise that is reduced thanks to the data analyzing step. The output signal produced by the proposed method is actually a chromatogram of interest related to one of the injected samples; it carries the same data as a single chromatogram acquired with a chromatography device wherein one single sample is injected in one single injection.

The proposed method results in a significant increase of the signal-to-noise ratio (SNR) in the output signal (chromatogram of interest), up to one order of magnitude or more, without requiring the use of a preconcentrator.

The proposed method allows multiple streams to be analyzed in parallel in a quasi-steady-state manner and in real time, whereas each time a new value is read from the detector, it can be used to update immediately the chromatograms corresponding to all the samples. Conveniently, this allows at any moment to obtain chromatograms without having to wait for the elution of all samples.

Since each sample is injected at times that are spread throughout the duration of the analysis (and not in "blocks" as taught by Trapp), our method enables more individual injections of each sample to be performed during the same time, thus improving the achievable signal-to-noise ratio.

The proposed method may comprise the following optional features in specific embodiments.

The step of cross-correlating may be performed for each sample. Each cross-correlation is performed between the recorded signal and a derived correlation function associated with a respective independent sample and produces a respective correlogram. The analyzing step may then be performed on each correlogram so as to obtain multiple output signals, each output signal being indicative of a composition of a respective sample. Therefore, many output signals may be produced from a common chromatogram signal acquired by the detector.

The pseudo-random binary sequences may be M-sequences, which have particular properties that allow reducing correlation noise contained in the correlograms.

The choice of M-sequences that are mutually "ideal" (i.e. having minimal 3-valued cross-correlations) provides minimal interference between the different sample streams.

The M-sequences may be chosen such that the cross-correlation function between any of the specific injection timing sequences and the derived correlation function associated to any other sample yields an amplitude that is lower than the amplitude of the cross-correlation function between any of the specific injection timing sequences with its own associated derived correlation function by a factor larger than 1.2, and preferably larger than 2, where the amplitude is defined as the difference between the maximum and the minimum values of a function. This factor may be chosen as large as possible.

The M-sequences may be chosen such that pairwise cross correlations are three-valued and the amplitude of these cross-correlations is as low as possible.

The M-sequence may be selected such that the pairwise cross-correlations have the lowest amplitude among the cross-correlation values of all the pairs of M-sequence of the same given length.

Besides, the different injection timing sequences of the said independent samples may overlap in time.

The injection timing sequence derived from each pseudo-random binary sequence may be repeated periodically in a circular manner at least one time.

Any cross-correlation operation between any of the specific injection timing sequences and its associated derived correlation function may yield a function with a high absolute value around time 0, preferably at time 0, compared to the other values in the rest of the signal.

Preferably, any cross-correlation operation between any of the specific injection timing sequences and its associated derived correlation function may yield a Dirac function centered at time 0

A correlogram obtained by cross-correlating a derived correlation function and the recorded signal theoretically shows a signal to noise ratio (SNR) that is $$\frac{M+1}{2\sqrt{M}}$$

times higher compared to a single-shot chromatogram, where M is the length (i.e. the number of elements) of the pseudo-random binary sequence.

The injection timing sequences associated with every sample may have the same duration and/or the same length.

Any injection timing sequence may inject sample during duration T=Mp wherein M is the length of the pseudo-random binary sequence and p is the duration allocated for injecting one fraction of sample. p is preferably chosen so that the total injection timing sequence duration T is greater than the longest expected single chromatogram duration of any individual sample being analyzed.

The longest expected single chromatogram duration corresponds to the longest duration that the sample may take in order to completely elute out of the column Each time interval of duration p may comprise a first time portion having a duration $\Delta t$ during which a fraction of the corresponding independent sample is either injected or not and a second time portion during which no injection is performed. The injection timing sequences corresponding to a first and a second sample are offset in time so that the first time interval portions of the first injection timing sequence occurs within the second time interval portions of the second injection timing sequence. Preferably, the injection timing sequences may be time-shifted so that the first time portions of any injection timing sequences occur within the second time portions of any other injection timing sequences.

One or more injection timing sequence may be time-shifted, wherein the same shift is applied to the signal derived from said pseudo-random binary sequence before the cross correlation with said recorded detector signal.

One or more injection timing sequence may be circularly permuted and the same circular permutation may be applied to the signal derived from said pseudo-random binary sequence before the cross correlation with the recorded detector signal.

Besides, the step of analyzing data of interest may comprise:
  determining a signal level separating a region of the correlogram with smaller signal levels consisting principally of noise data, and a region of the correlogram signal containing higher signal levels in the form of peaks carrying data of interest; and
  filtering out the region of smaller signal by thresholding the correlogram signal at the determined signal level, in order to obtain an improved correlogram signal.

The step of analyzing data of interest may comprise smoothing the improved correlogram signal in order to avoid sharp edges of the peaks.

The step of analyzing data of interest may further comprise:
  computing a refined version of said individual correlogram signal using another individual correlogram signal, wherein said another individual correlogram signal is used as an input of the step of analyzing data of interest.

The refined version of the i-th individual correlogram, where the correlation noise from the j-th sample is reduced, may be the result of the following formula:

$$(b_i - (m'_i \otimes m_j) * \sigma(b_j)/\alpha)$$

wherein:
  $b_i = m'_i \otimes s$ is the correlogram associated to sample i
  $\alpha$ is a scaling coefficient
  s is a portion of duration T of the signal recorded by the detector
  $\sigma(b_j)$ is a filtered version of the chromatogram corresponding to sample j,
  $m'_i$ is the derived correlation function associated to the injection timing sequence $m_i$,
  $m_j$ is the timing injection sequence of sample j
  $\otimes$ is a circular correlation operator, and
  * is a circular convolution operator.
  In particular, $\alpha$ may be $(M+1)/2$.

The computing step may be repeated multiple times, each time resulting in a better approximation of the individual chromatograms.

The analysis step may be performed in real time, using the data from a moving time window of duration at least equal to the duration of the longest of said specific injection timing sequences.

The method may also comprise estimating a data of interest/correlation noise ratio for each correlogram before computing the refined version of said individual correlogram, said another individual correlogram signal being selected as the correlogram having a highest data of interest/correlation noise ratio.

The step of analyzing data of interest may be performed in real time, using the data from a moving time window having a duration at least equal to a duration of the longest of the specific injection timing sequences.

According to a second aspect, the invention relates to a chromatography device for analyzing at least two samples simultaneously using the method according to the first aspect of the invention.

The chromatography device comprises
a manifold comprising a plurality of inlets for injecting fractions of samples and an outlet,
a plurality of injectors, each injector being arranged at a corresponding inlet for selectively injecting a fraction of fluid sample from said inlet,
a control unit configured for controlling the state of each injector according to a specific injection timing sequence derived from a pseudo-random binary sequence,
a chromatography column connected at the outlet of the manifold,
a detector placed at the outlet of the chromatography column and configured to acquire a signal for a period of time at least equal to a duration of a longest of said specific injection timing sequences; and
a signal processing unit configured to:
cross-correlating the signal acquired by the detector and a derived correlation function, said derived correlation function being derived from the pseudo-random binary sequence associated with said sample, so as to obtain an individual correlogram signal specific to the sample; and
analyzing data of interest of the individual correlogram signal so as to obtain an independent output signal indicative of the composition of the sample.

The chromatography column may be a gas chromatography column or a liquid chromatography column.

According to a third aspect, the invention also relates to a system for analyzing air in different areas of a building, the system comprising the chromatography device according to the second aspect of the invention and a plurality of pipelines, each pipeline being arranged to collect air from a respective area of the building and deliver the collected air to a respective inlet of the chromatography device.

BRIEF DESCRIPTION OF THE DRAWINGS

Further details, features and advantages of the invention are explained in more detail below with the aid of the exemplary embodiments of the invention that are illustrated in the figures in which:

FIG. 1B shows a chromatography device according to a second embodiment of the invention.

FIG. 2A shows a pseudo-random binary sequence of length M=7.

FIG. 2B shows injection timing functions derived from the pseudo-random binary sequence of FIG. 2A.

FIG. 2C shows correlation functions derived from the pseudo-random binary sequence of FIG. 2A.

FIG. 6 shows sub-steps of filtering steps shown in FIG. 5.

FIG. 7 shows two signals obtained when running steps of FIG. 6.

Similar features have identical numbers in all figures.

DETAILED DESCRIPTION OF PREFERRED EMBODIMENTS

Figure 1A:
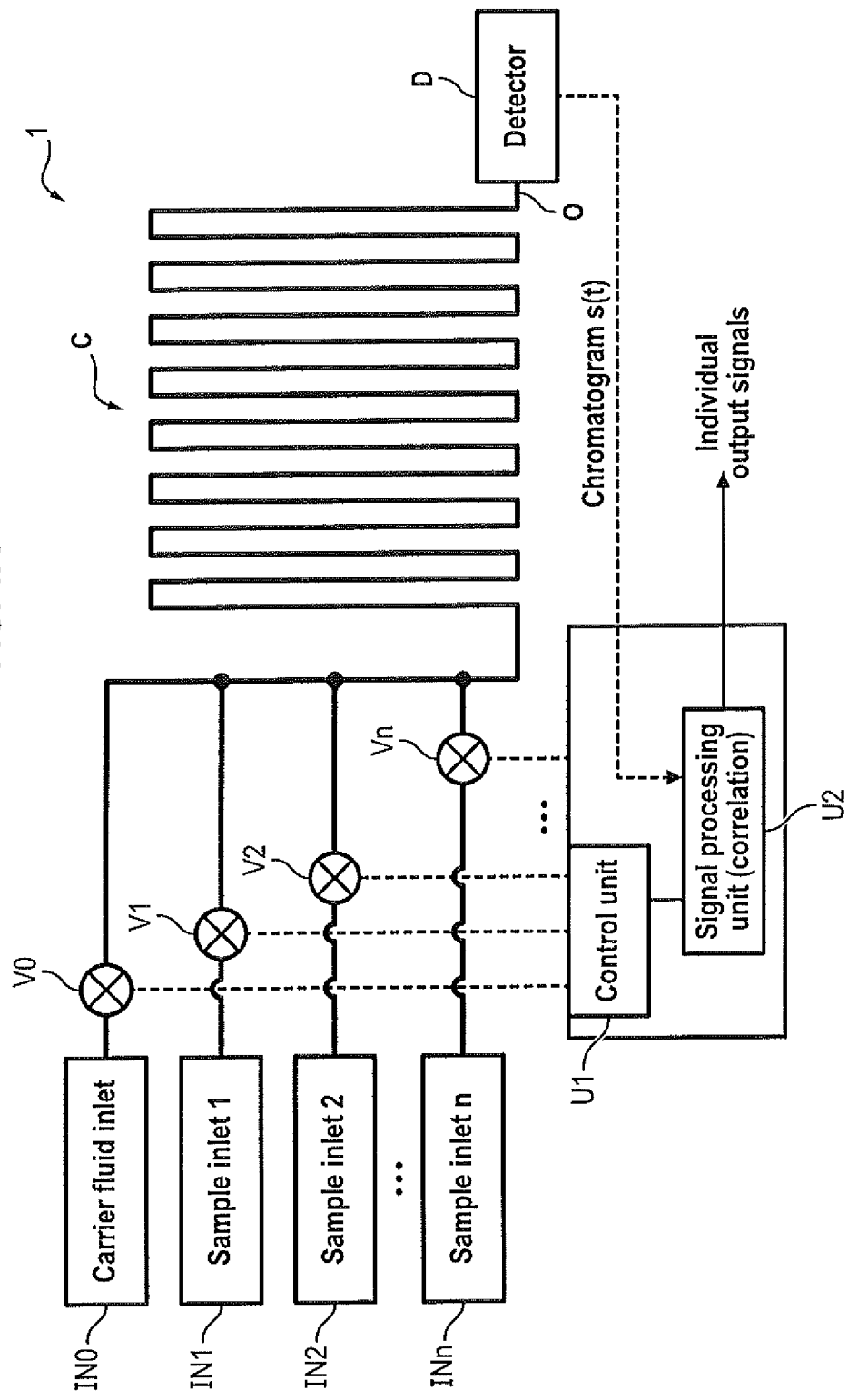
FIG. 1A shows a chromatography device according to a first embodiment of the invention.

FIG. 1A shows a first embodiment of a chromatography device 1 for analyzing n independent samples simultaneously.

The chromatography device 1 comprises a plurality of sample inlets IN1 to INn, each sample inlet INi being designed for inputting a respective fluid sample hereafter referred to as "sample". The device 1 may also comprise an additional carrier inlet INC designed for inputting a carrier fluid for carrying the samples inputted through inlets IN1 to INn.

Different types of samples may be inputted through each inlet IN0-In: a gas or a liquid.

The device 1 also comprises a plurality of on-off valves V0-Vn, each valve $V_i$ acting as an injector arranged at a corresponding inlet INi for selectively opening and closing the inlet INi.

The device 1 also comprises one outlet O connected to all sample inlets IN0-INn, and a chromatography column extending between the inlets and the single outlet O. Thus, fluidic samples coming from inlets IN1 to INn carried thanks to the carried fluid coming from inlet IN0 can enter the chromatography column C as a fluid mixture.

The chromatography column C is configured to separate different analytes contained in the fluid mixture during its propagation towards the single outlet. Such column is known of the man skilled in chromatography; it will not be described in detail hereafter.

Different types of injectors may be included in the chromatography device according to the invention.

In a first embodiment depicted on FIG. 1A, 2-ways on-off valves are used as injectors. Each sample inlet is connected to an input of a valve, and all outputs are connected to the column C. The carrier gas line may also be controlled through the use of an on-off valve or a flow regulator. The gas flows may be controlled by over pressuring the gas inlets or pumping at the outlet or both. The injection of a given sample in the system is performed through the opening of the corresponding valve during a given time portion Δt. The value of Δt may be different for each valve.

In a second embodiment depicted on FIG. 1B, multi-port rotary valves are used as injectors in series operation. In this operation mode, the carrier gas line is shared by all the injectors. That means that when a sample is injected upstream, the said sample goes through all the valves before reaching the column. Each valve is controlled independently by the control unit.

Figure 1C:
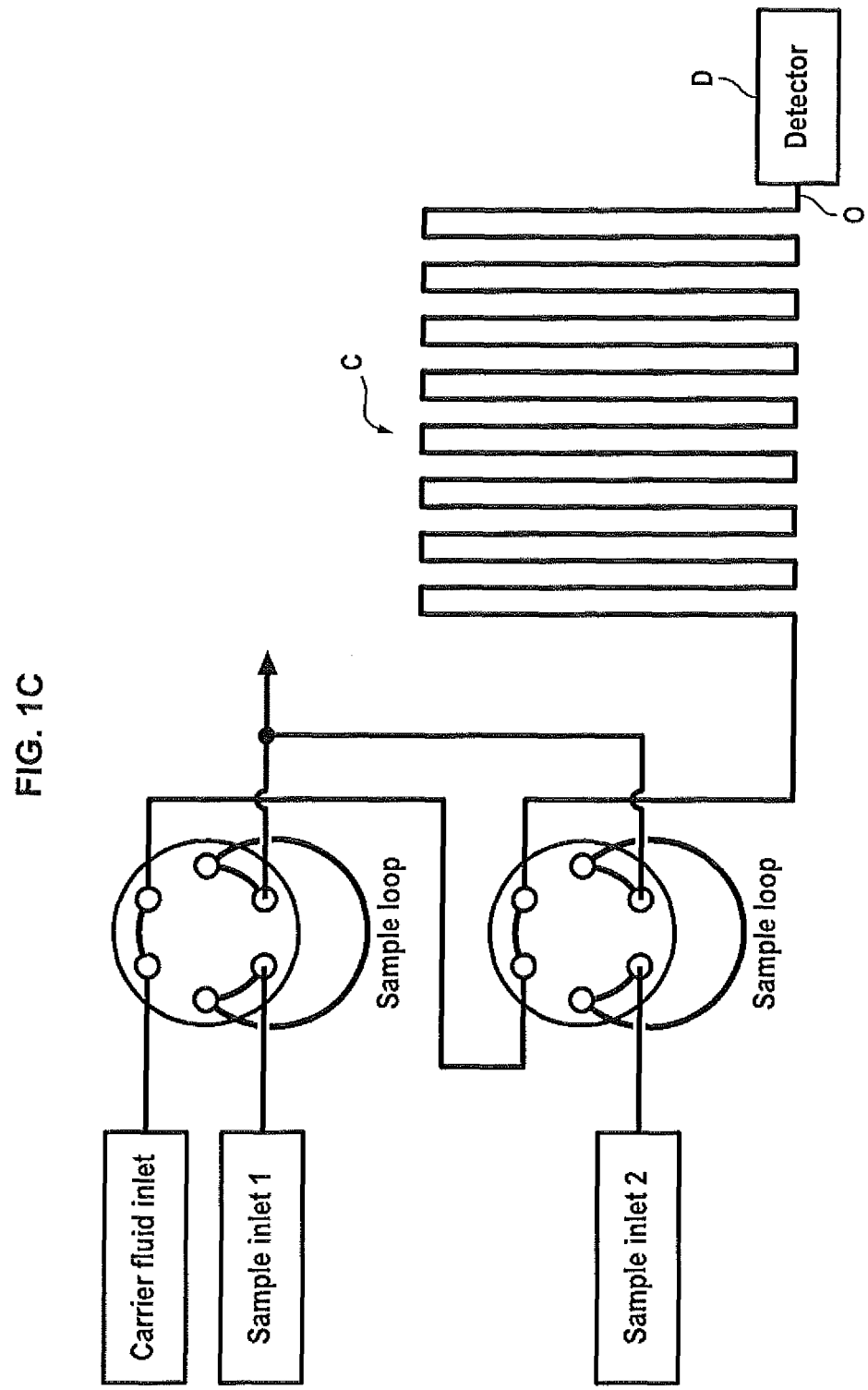
FIG. 1C shows an injection part of a chromatography device according to a third embodiment of the invention.

In a third embodiment depicted on FIG. 1C, presents an example of an injector in series operation based on two 2-position 6-port rotary valves using a sample loop. Such rotary valves are often used to inject a controlled amount of gas corresponding to the internal volume of the sample loop: in their normal position, the gas vector flows directly to the output while the sample flows in the sample loop. When the position of the valve is switched, the carrier gas flows through the sample loop and pushes the sample to the output. In this example, the carrier gas line is connected to a first rotary valve, and the output of this first rotary valve is then connected to the carrier gas input of the second valve. When the position of any valve is switched, the sample present in the corresponding sample loop is pushed to the column. In this configuration, one must be careful to operate the valve so that no sample injected upstream is disturbed by the switching of a valve downstream.

Figure 1D:
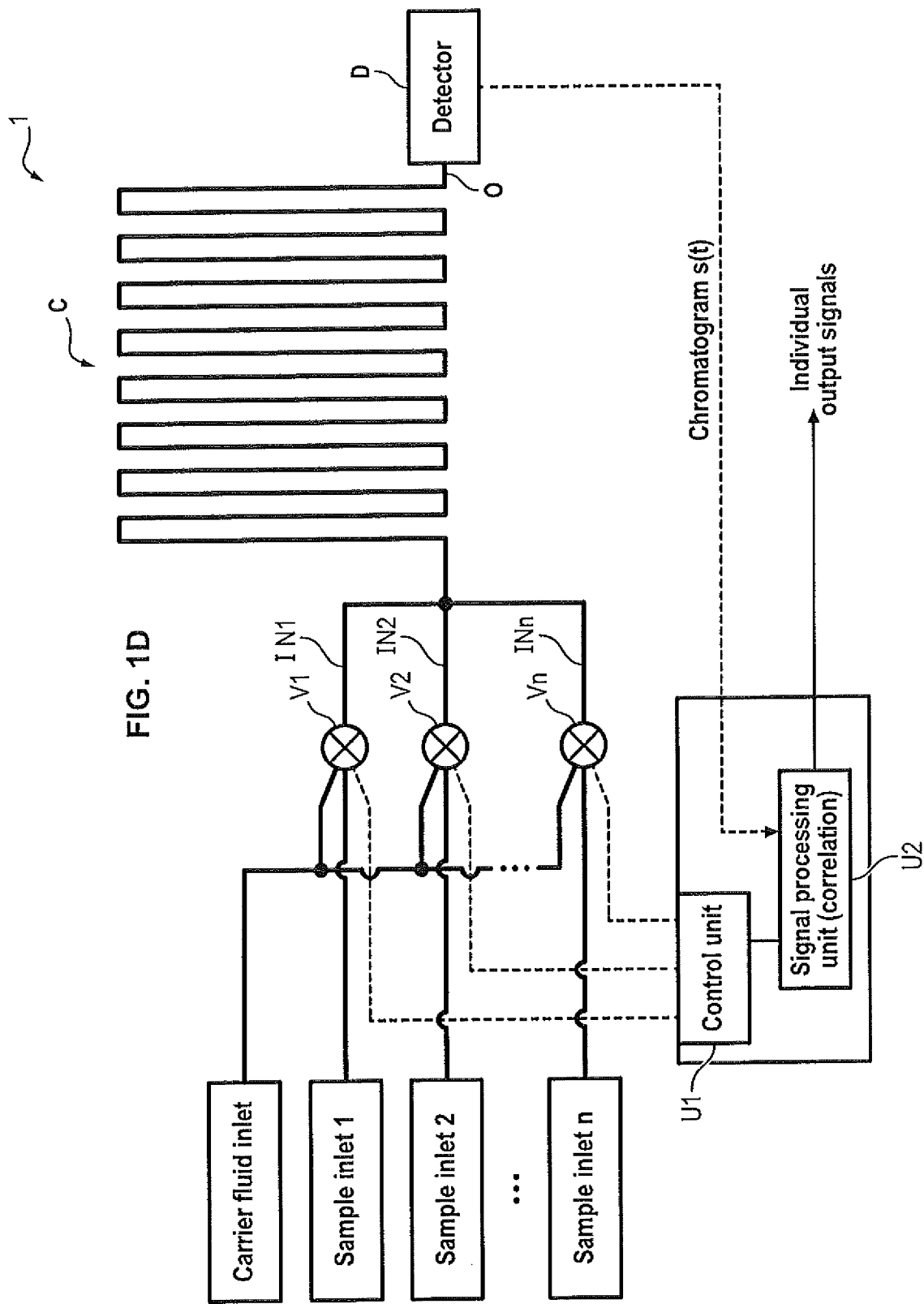
FIG. 1D shows a chromatography device according to a fourth embodiment of the invention.

In a fourth embodiment depicted on FIG. 1D, multi-port rotary valves are used in parallel operation. In this operation mode, the carrier gas line is split between all the valves. The output of each valve is then connected to the column. Each valve is controlled independently by the control unit.

Figure 1E:
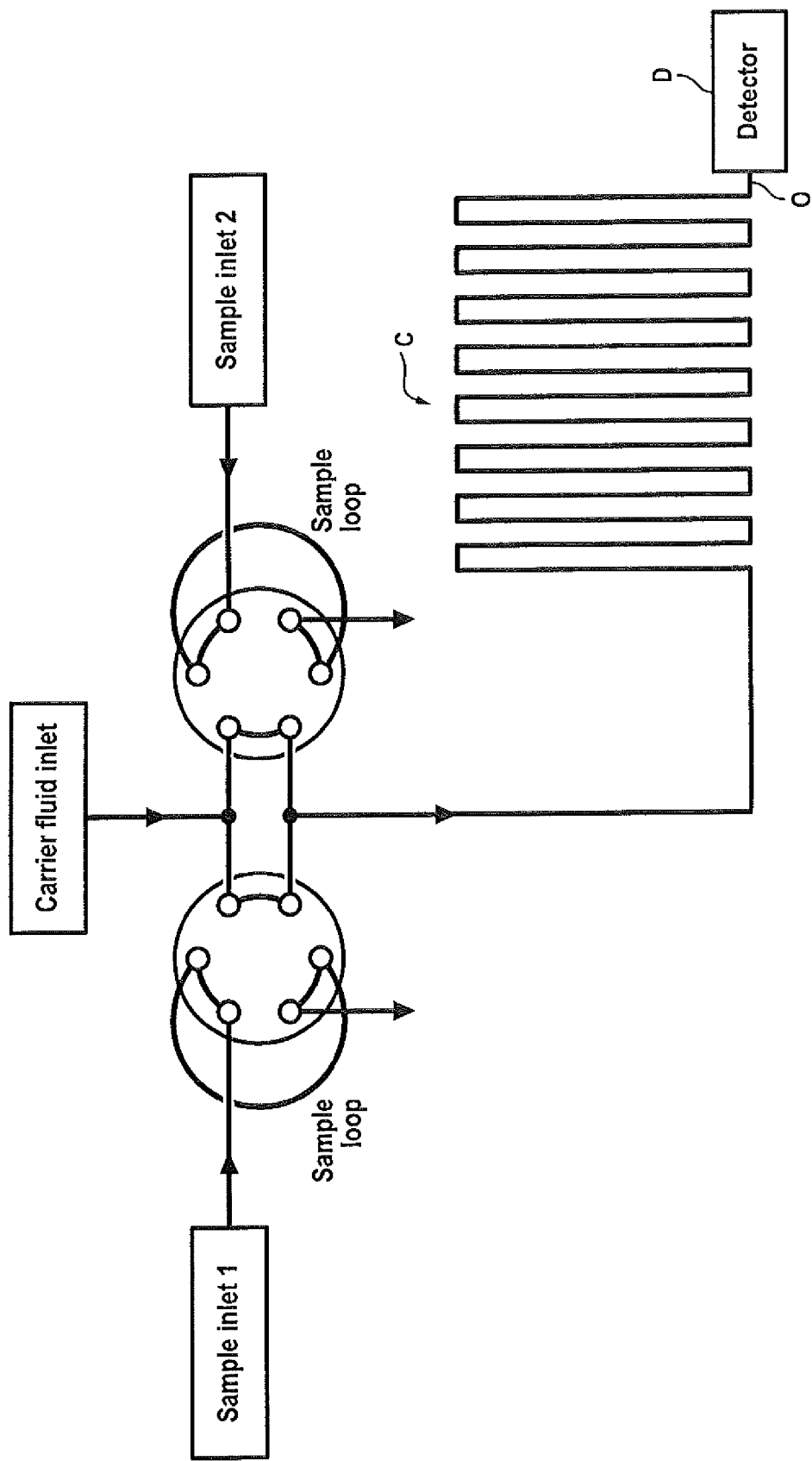
FIG. 1E shows an injection part of chromatography device according to a fifth embodiment of the invention.

A fifth embodiment depicted on FIG. 1E presents an example of an injector in parallel operation based on two 2-position 6-port rotary valves using a sample loop. In a similar way to the embodiment depicted on FIG. 1C, the position switching of any valve allows injecting a given volume of gas. Here, each sample may be injected regardless the previous injections due to the fact that the samples directly flows to the column that makes this configuration more adapted to the multiple injection technique.

Any combination of these operation modes may be used and any other combination of any injector may be used as long as it can independently inject controlled amounts of multiple samples.

The chromatography device 1 also comprises a detector D placed at the outlet O. The detector D is configured to acquire a signal s(t) named hereafter "chromatogram" which contains data of interested related to the multiple samples injected thanks to injectors V1 to Vn. In an embodiment, the detector D is a flame ionization detector (FID). In another embodiment, the detector D is a thermal conductivity detector (TCD).

The chromatography device 1 also comprises a control unit U1 configured for controlling the opening of each injector V0-Vn according to an injection timing sequence. Each injector is associated with a respective injection timing sequence.

The chromatography device 1 further comprises a signal processing unit U2 configured to process the chromatogram s(t) acquired by detector D so as to obtain n individual output signals according to a method that will be described below, each output signal containing data of interest related with a respective injected sample.

The chromatography device is preferably designed as a micro chromatograph (GC) which has the great advantage of being small-sized and possibly batch-fabricated, thus much more portable than their bulky laboratory counterparts.

In an exemplary embodiment, the chromatography device comprises a table-top Agilent 6890 chromatograph equipped with a 25 m-long Varian CPSIL chromatography column. Two individual samples are injected using two VALCO 6-port 2-position rotary valve injectors with a 10 μL sample loop; volatile organic compounds (VOCs) are inputted through inlets IN1-IN2, such as BTEX (Benzene, Toluene, Ethylbenzene, m/p-Xylenes) diluted in nitrogen, and the carrier fluid is helium. Flow is assured by pressurizing the carrier and sample gas inlets.

Each injection timing sequence m1(t), m2(t) (associated with a respective injector) is derived from a respective pseudo-random binary sequence.

In a preferred embodiment, the different pseudo-random binary sequences are M-sequences.

A M-sequence of order N (N being an integer number) is a binary sequence of integers that can take the value −1 or +1. M defines the "length" of the M-sequence m(t) and equals $M=2^N-1$. The exemplary M-sequence μ illustrated in FIG. 2A has order 3, length 7 and values $\{+1, -1, -1, +1, +1, +1, -1\}$.

The M-sequence function μ has a compact autocorrelation support, i.e it fulfills the following formula:

$$(\mu \otimes \mu)[i] = \sum_{j=0}^{M-1} \mu[j]\mu[(i+j) \bmod M] = \begin{cases} M, \text{ if } i = 0 \\ -1, \text{ if } i \neq 0 \end{cases}$$

Wherein μ[i] refers to the value of the i-th integer of the M-sequence.

FIG. 2B shows an injection timing sequence based on μ in both continuous and discrete format. In practice, signals are recorded with a sampling period δt. Thus, each element of a discrete signal corresponds to a duration δt in the corresponding continuous signal. Any computation is then performed based on discrete signals.

Here, we define "p" as the time between two consecutive injections, and "T" as the total duration of the injection timing sequence such that T=Mp. "p" should be chosen such that it is a whole multiple of the sampling period δt.

The signal m(t) is defined preferentially as follows: this function has a period divided into M time intervals of duration "p". Each time interval corresponds to a value of the M-sequence μ. If the value of μ is 1, the corresponding time interval's value of m(t) is 1 for a duration δt and 0 for the rest of the time interval. If the value of μ is −1, the value of m(t) is 0 for the whole corresponding time interval. The discrete signal m[i] is then deduced from the relationship between a continuous signal and its discrete version.

The injection timing sequence m(t) can be derived into a correlation function m'(t) which is depicted in FIG. 2C in both continuous and discrete format.

The derived correlation function is computed the same way as the injection timing sequence except that if the value of M-sequence μ is −1, the corresponding time interval's value of m'(t) is −1 for a duration δt and 0 for the rest of the time interval. A discrete signal m'[i] corresponding to the derived correlation function is then deduced from the relationship between a continuous signal and its discrete version.

The signals m[i] and m'[i] are used during a method that will be described later on in the present document.

Also, the signal m[i] is used by the injector control unit U1 to command the injection of a sample in the column C. If the value of m[i] changes from 0 to 1, the corresponding injector is actuated by the control unit U1 to inject a fraction of sample during a predetermined duration Δt that should not be longer than p. As a result the function m[i] allows up to M fractions of the same sample to be injected or not by the associated injector, each fraction of the sample being injected during the duration $\Delta t$. $\Delta t$ may depend on the specific drive signal applied to an injector but also on the specific geometry and configuration of the injector. For example, in the case of a 2-position 6-port rotary valve, $\Delta t$ may be chosen such that the whole volume of sample gas present in the sample loop is carried away to the output of the valve. $\Delta t$ may be preferably chosen as short as possible in order to be able to inject all the samples with an offset in time within the same time portion p. $\Delta t$ may be preferably chosen such that $\Delta t <= p/n$ where n is the number of samples to be analyzed in parallel.

Figure 2D:
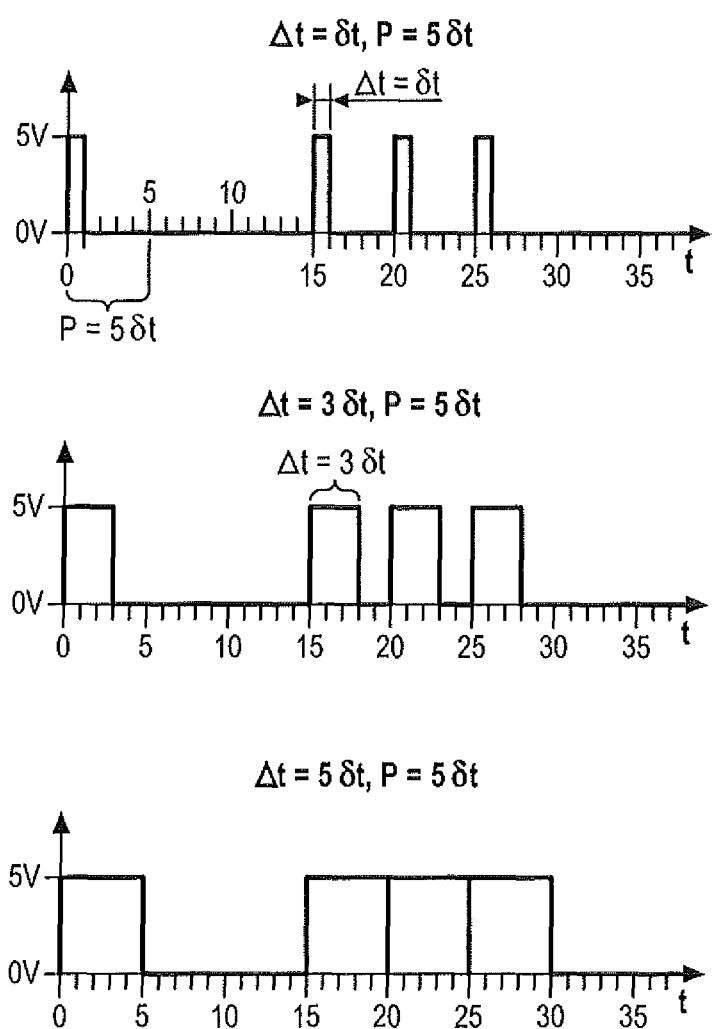
FIG. 2D shows driving voltage signals associated with the pseudo-random binary sequence of FIG. 2A.

FIG. 2D shows examples of driving voltage signals used for the given example that commands on-off valves based on the injection timing sequence depicted in FIG. 2B, for different values of injection time $\Delta t$. The voltage signal commands the opening state of an on-off valve that is open when the voltage is 5V and that is closed when the voltage is 0V. This signal allows the injection during a time portion $\Delta t$ that is preferably a whole multiple of the sampling frequency $\delta t$.

An interesting property of the function m(t) and the derived correlation function m'(t) may be:

$$m'(t) \otimes m(t) = \propto \delta(t)$$

wherein $\delta$ is the Dirac function and $t \in [t0, t0+]$, where $t0$ is an arbitrary time, $\otimes$ is the circular cross-correlation operator and $\propto$ is a constant.

The role played by this derived correlation function m'(t) will be explained later on.

In the following, each injector $V_i$ is associated with a respective M-sequence of function mi(t) and a derived correlation function mi'(t).

If the column C does not saturate and the detector D response is linear, which is verified most of the time when concentrations are low, the chromatography device 1 behaves like a linear system. From a signal processing point of view, the column C and the detector D may be regarded as a linear system having an impulse response s0(t) which corresponds to the chromatogram of a single injection of the sample. Such linear system is represented as a dashed box in FIGS. 3A and 3B.

Figure 3A:
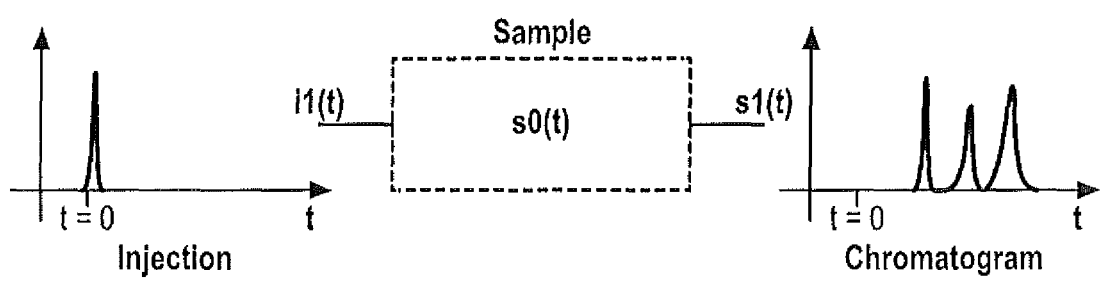
FIG. 3A represents a model of the chromatogram seen as a linear system with an impulse response s0(t).

FIG. 3A represents the model of a linear chromatography device wherein one single fraction of one sample is injected. A chromatograph s(t) acquired in output of such device is the following:

$$s1(t) = (i1 * s0)(t)$$

wherein i(t) is an elementary injection signal that corresponds to a signal associated to a given injector and a given injected amount of gas and * is the convolution operator.

If multiple samples are simultaneously injected in a single linear chromatography column the resulting chromatogram s(t) is the sum of the chromatograms corresponding to each individual sample injection.

Figure 3B:
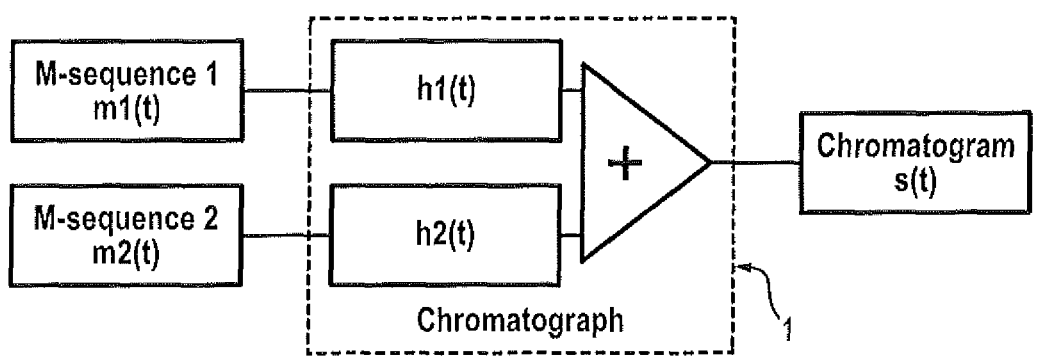
FIG. 3B represents a mathematical model of a chromatography device according to an embodiment of the invention comprising 2 sample inlets.

For instance, the chromatography device 1 for analyzing two samples 1 and 2 (n=2) is functionally represented on FIG. 3B. In such embodiment, the injector V1 is controlled by the function m1(t) and the injector V2 is controlled by the function m2(t). If this device 1 is linear, the chromatogram s(t) is the following:

$$s(t) = (m1 * s1)(t) + (m2 * s2)(t)$$

wherein:
* is the convolution operator,
s1 is a chromatogram of interest corresponding to sample 1.
s2 is a chromatogram of interest corresponding to sample 2.

For simultaneous single-injection of two analytes, it may be difficult to know the origin of a given datum of interest in the chromatogram s(t) because the summation operation that occurs in the column does not preserve information on sources. However, the particular properties of M-sequences may be used to overcome this issue so that independent sample streams can be analyzed using a single chromatography device so as to produce the chromatogram of interest s1 and s2.

Figure 4:
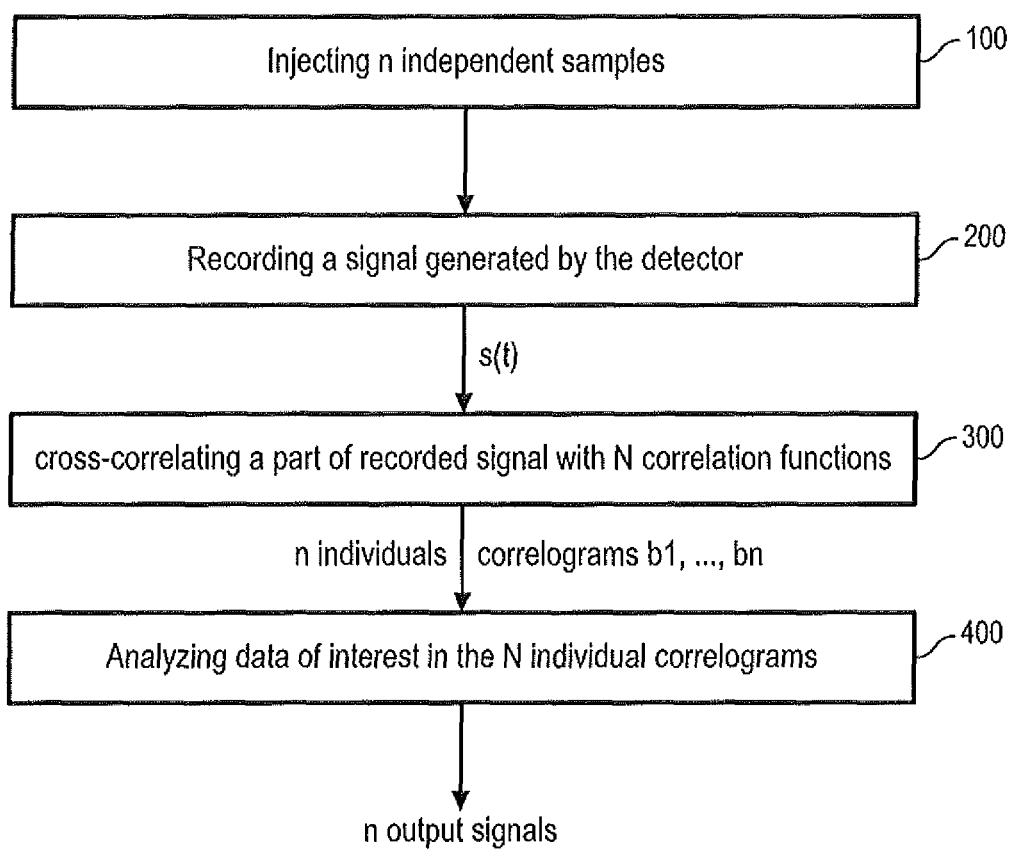
FIG. 4 shows the steps of a method for analyzing multiple samples according to an embodiment of the invention.

An embodiment of a method for analyzing n samples using the chromatography device 1 will now be described in relation with FIG. 4. A purpose of such method is to obtain for each sample i a corresponding chromatogram of interest si.

In a step 100, each injector $V_i$ is controlled by the control unit U1 according to its associated timing injection sequence mi(t). Each timing injection sequence mi(t) is repeated periodically over time; in other words, the mi(t) defines the period of a periodic signal.

All M-sequences may the same length M and their associated injection functions may have the same duration T or not. If some associated injection functions have different durations, T is assumed to be the longest duration. During T, one or many fractions of each sample is injected.

The different injection timing sequences mi(t) of the different independent injected samples may overlap in time (i.e at least one fraction of a first sample and at least one second fraction of a second sample are injected simultaneously during $\Delta t$ or less).

Injected samples get mixed with the carrier fluid as a mixture which enters the chromatography column C and reaches the outlet O after being separated into analytes by the column C.

In a step 200, the detector D placed at the outlet O generates a chromatogram s(t) from the separated mixture. The chromatogram s(t) is recorded by the signal processing unit U2 preferably for the duration T of the longest timing function, preferably when the signal recorded has reached a quasi-periodic state due to the cyclic injection patterns.

In a step 300, the signal processing unit U2 uses performs n cross-correlation operations based on the signal s(t).

For each sample i, the cross-correlation operation between the signal s(t) and the derived correlation function mi'(t) associated with sample i inputted through inlet INi produces an individual correlogram signal bi(t) associated to sample 1 using the following computation:

$$bi = m'_i \otimes s$$

wherein $\otimes$ is a circular cross-correlation operator. An example of circular cross-correlation operator on signals u, v is the following:

$$(u \otimes v)[i] = \sum_{j=0}^{M-1} u[j]v[(i+j) \bmod M]$$

Correlogram signals b1, . . . , bn are referred to as "correlograms" in the following for the sake of simplicity.

If the cross-correlation of a function $m_i(t)$ and the derived function $m'_i(t)$ is not an exact Dirac function, some correlation noise is introduced in correlogram bi(t) which is however of lower order of magnitude than the original signal. The correlogram bi(t) theoretically shows a signal to noise ratio (SNR) that is $$\frac{M+1}{2\sqrt{M}}$$

times higher compared to a single-shot chromatogram.

For each sample i, the correlogram bi carries data related to the composition of said sample i, which are regarded as data of interest. These data of interest appear in the correlogram i as peaks. However, the correlogram bi also contains additional noise data which may prevent the data of interest to be correctly viewed in the correlogram.

Assuming n=2, the cross-correlation associated with sample 1 may be written as follows:

$$b1 = m'1 \otimes s = m'1 \otimes (m1*s1 + m2*s2) = \propto s1 + (m'1 \otimes m2)*s2$$

wherein $\propto = (M+1)/2$.

In this equation the first term preceded with coefficient $\propto$ carries data of interest (chromatogram of interest s1) and the second term depending of the other signal s2 is regarded as correlation noise. This second term could be subtracted from signal b1 if s2 was perfectly known.

Similarly, $$b2 = \propto s2 + (m'2 \otimes m1)*s1$$

In this equation the first term preceded with coefficient $\propto$ carries data of interest (chromatogram of interest s2) and the second term depending of the other signal s1 is regarded as correlation noise. This second term could be subtracted from signal b1 if s2 was perfectly known.

Of course, if more n>2 samples are injected, second terms depend of n−1 other samples.

In an embodiment, the cross-correlation of step 300 is performed thanks to a FFT-based technique (Fast Fourier Transform).

In another embodiment the M-sequences are generated with a linear feedback shift-register-based algorithm.

In a step 400, each correlogram bi is analyzed so as to obtain the corresponding output signal (chromatogram of interest si). In this output signal si, data of interest associated with the sample i is isolated from noise (this noise includes data of interest associated with any other injected sample).

Figure 5:
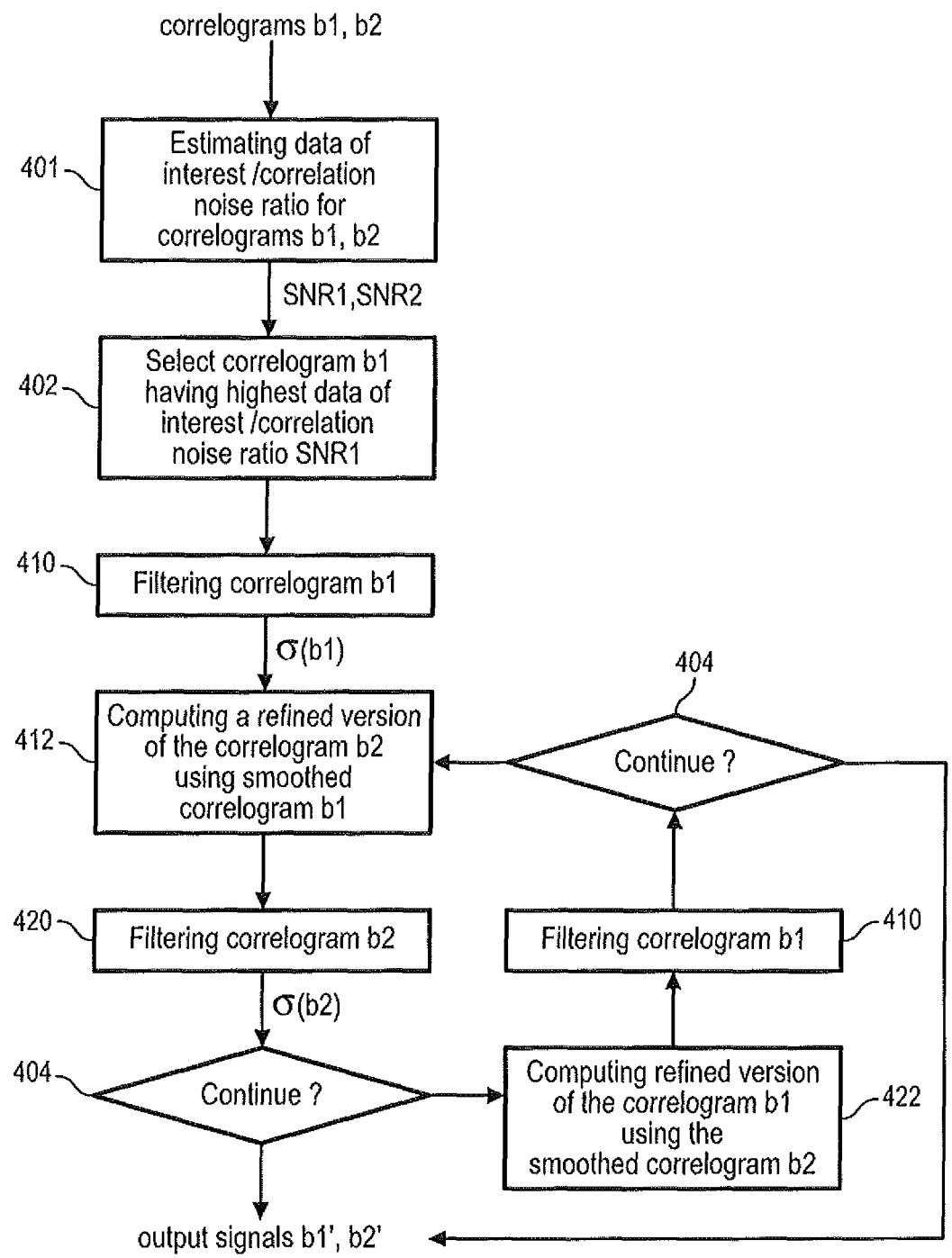
FIG. 5 shows sub-steps of the analyzing step shown in FIG. 4.

An embodiment of step 400 is illustrated on FIG. 5. In this embodiment, a pair of correlograms b1, b2 is processed thanks to the following sub-steps.

In a filtering step 410, the signal processing unit U2 filters the correlogram b1 so as to obtain a filtered correlogram σ(b1). This filtered correlogram is therefore regarded as a "good" approximation of the chromatogram of interest s1:

$$s1 \cong \frac{\sigma(b1)}{\propto}$$

Similarly, in a filtering step 420, the signal processing unit U2 filters the correlogram b2 so as obtain a filtered correlogram σ(b2). This filtered correlogram is an approximation of the chromatogram of interest s2:

$$s2 \cong \sigma(b2)/\propto$$

Filtering steps 410 and/or 420 may typically comprise the following sub-steps (which are illustrated in FIG. 6).

In a correlogram bi to be filtered, the signal processing unit U2 determines 601 a signal level separating a region of the correlogram with smaller signal levels consisting principally of noise data, and a region of the correlogram signal containing higher signal levels in the form of peaks carrying data of interest (this signal level a dashed line in the exemplary correlogram illustrated on top of FIG. 7).

The signal processing unit U2 then thresholds 602 the correlogram bi according to the signal level determined in step 601, using known techniques. In the thresholded correlogram bi, all noise data contained in the lower region of the correlogram bi is removed.

In a step 603, the thresholded correlogram bi may be smoothed so as to remove sharp edges from said correlogram. An exemplary filtered correlogram is depicted at bottom of FIG. 7.

In the embodiment shown in FIG. 5 filtering steps 410 and 420 are performed sequentially and are preceded by a preliminary step 401 and 402.

In step 401, the signal processing unit 112 estimates a data of interest/correlation noise ratio SNR1 for correlogram b1, and a data of interest/correlation noise ratio SNR2 for correlograms b2. Such ratios may in practice be signal amplitude to noise amplitude ratios.

Then, in step 402, the signal processing unit U2 selects the correlogram having the highest data of interest/correlation noise ratio, for example b1 (SNR1>SNR2).

The filtering step 410 is then performed on selected correlogram b1.

In a step 412, the signal processing unit U2 computes a refined version of the other correlogram b2 which is the result of the following formula:

$$(b2 - (m'2 \otimes m1)*\sigma(b1)/\alpha)$$

wherein α is a scaling coefficient equal to (M+1)/2 in order to fit with the cross-correlation second term described upward.

This computation allows subtracting in correlogram b2 the cross-correlation noise that was initially present due to the large signal corresponding to sample 1. In the refined version of b2 the correlation noise associated with sample 1 (the second term mentioned of b2 upwards) is therefore reduced.

The filtering step 420 is then performed on the refined version of correlogram b2 so as to obtain a signal σ(b2).

From this point on, signals σ(b1) and σ(b2) can be used as output signals. However, the filtered signal σ(b2) may advantageously be used again in the computing 422 of a refined version of the correlogram b1 so as to produce another version of the correlogram b1 in which the correlation noise associated with sample 2 is reduced.

The obtained refined version of the correlogram b1 may then be filtered again in step 410.

The sequence consisting of steps 412, 420, 422 and 410 may be repeated multiple times. Each iteration of this sequence produces refined new versions of the correlograms b1, b2 from which more noise is removed.

Each iteration of the loop may comprise a step 404 between steps 420 and 422, and/or between steps 410, 412, wherein the signal processing unit U2 checks if a predetermined condition is fulfilled. As long as the condition is not fulfilled the sequence continues; when the condition is fulfilled, current versions of the correlograms b1, b2 are regarded as sufficiently cleaned up. This condition may for instance be a predetermined signal to noise ratio value to be reached so as to end the loop.

Processing first the correlogram having the highest SNR ratio is particularly advantageous if samples 1 and 2 are unbalanced (at least one of the signals bi is then completely dwarfed by correlation noise).

The steps comprising the embodiment illustrated in FIG. 5 for a pair of correlograms may be performed for a n-uplet of correlogram.

If there are n correlograms signals, the signal bi having the highest signal to noise ratio SNRi should be subtracted from the (n−1) other signals, and then the process should be repeated.

The method described upwards may be implemented in multiple types of chromatography devices 1: gas chromatographs or liquid chromatographs.

The chromatography device 1 may be utilized for various purposes.

Figure 8:
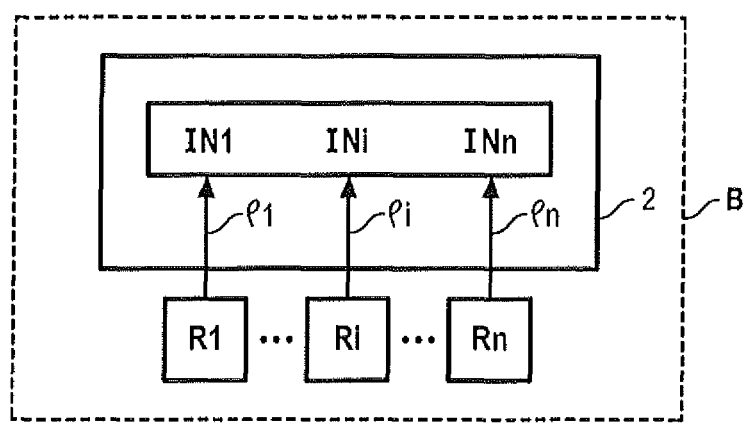
FIG. 8 is a system embedding the chromatography device illustrated in FIG. 1.

An example of application of such device method is the system 2 illustrated on FIG. 8.

The system 2 is for analyzing air in different areas R1, . . . , Rn of a building B.

This system 1 comprising the chromatography device 1 and a plurality of pipelines P1 to Pn. Each pipeline Pi is arranged to collect air from a respective area Ri of the building B (for instance a respective room of the building B).

Each pipeline Pi is also arranged to deliver the collected air so as samples of it can be injected into a respective inlet INi of the chromatography device 1.

The invention claimed is:

1. A method for simultaneously analyzing at least two samples using a chromatography device comprising a chromatography column having an inlet and an outlet, and at least one detector placed at the outlet of the chromatography column, the method comprising steps of:
    injecting fractions of each independent sample at the inlet of the chromatography column, the fractions of each independent sample being injected according to a specific injection timing sequence derived from a pseudo-random binary sequence associated with said independent sample;
    recording a signal generated by said detector for a period of time at least equal to a duration of the longest of the specific injection timing sequences;
    cross-correlating the recorded signal and a derived correlation function, said derived correlation function being derived from the pseudo-random binary sequence associated with one of the independent samples, so as to obtain an individual correlogram signal specific to said independent sample; and
    analyzing data of interest of the individual correlogram signal so as to obtain an output signal indicative of a composition of the sample.

2. The method of claim 1, wherein the different injection timing sequences of the independent samples overlap in time.

3. The method of claim 2, wherein cross-correlating any of the specific injection timing sequences and its associated derived correlation function yields a function having a high absolute value around time 0 compared to the other values in the rest of the signal.

4. The method of claim 1, wherein the pseudo-random binary sequences are M-sequences.

5. The method of claim 4, wherein the M-sequences are chosen such that cross-correlating any of the specific injection timing sequences and the derived correlation function associated to any other sample yields an amplitude that is lower than the amplitude of the cross-correlation function between any of the specific injection timing sequences with its own associated derived correlation function by a factor larger than 1.2.

6. The method of claim 5, wherein the M-sequences are chosen such that pairwise cross correlations are three-valued.

7. The method of claim 6, further comprising estimating a data of interest/correlation noise ratio for each correlogram before computing the refined version of said individual correlogram, said another individual correlogram signal being selected as the correlogram having a highest data of interest/correlation noise ratio.

8. System for analyzing air in different areas of a building, the system comprising the chromatography device of claim 7 and a plurality of pipelines, each pipeline being arranged to collect air from a respective area of the building and deliver a fraction of the collected air to a respective inlet of the chromatography device.

9. The method of claim 4, wherein the M-sequences are selected such that the pairwise cross-correlations have the lowest amplitude among the cross-correlation values of all the pairs of M-sequence of the same given length.

10. The method of claim 1, wherein the injection timing sequence derived from each pseudo-random binary sequence is repeated periodically in a circular manner at least one time.

11. The method of claim 1, wherein the injection timing sequences associated with every sample have the same duration.

12. The method of claim 1, wherein the pseudo-random binary sequences associated with every sample have the same length.

13. The method of claim 1 wherein, when the injection timing sequence duration is T=Mp where M is the length of the pseudo-random binary sequence and p is the time interval corresponding to the delay between two injections, and where p is chosen so that the total injection timing sequence duration T is greater than the longest expected single chromatogram duration of any individual sample being analyzed.

14. The method of claim 13, wherein each time interval p comprises a first time interval portion during which a fraction of the corresponding independent sample is either injected or not and a second time interval portion during which no injection is performed.

15. The method of claim 14, wherein the injection timing sequences corresponding to a first and a second sample are time-shifted so that the first time interval portions of the first injection timing sequence occurs within the second time interval portions of the second injection timing sequence.

16. The method of claim 15, wherein one or more injection timing sequence is time-shifted and wherein the same shift is applied to the signal derived from said pseudo-random binary sequence before the cross correlation with said recorded detector signal.

17. The method of claim 1, wherein one or more injection timing sequence is circularly permuted and wherein the same circular permutation is applied to the signal derived from said pseudo-random binary sequence before the cross correlation with said recorded detector signal.

18. The method of claim 1, wherein the step of analyzing data of interest comprises:
    determining a signal level separating a region of the correlogram with smaller signal levels consisting principally of noise data, and a region of the correlogram signal containing higher signal levels in the form of peaks carrying data of interest; and
    filtering out the region of smaller signal by thresholding the correlogram signal at the determined signal level, in order to obtain an improved correlogram signal.

19. The method of claim 18, wherein the step of analyzing data of interest comprises smoothing the improved correlogram signal.

20. The method of claim 18, wherein the step of analyzing data of interest further comprises:
    computing a refined version of the individual correlogram signal using another individual improved correlogram signal, wherein said another individual improved correlogram signal is used as an input of the step of analyzing data of interest.

21. The method of claim 1, wherein the step of analyzing data of interest further comprises:
computing a refined version of the individual correlogram signal using another individual correlogram signal, wherein said another individual correlogram signal is used as an input of the step of analyzing data of interest.

22. The method of claim 21, wherein the refined version of the i-th individual correlogram, where the correlation noise from the j-th sample is reduced, is the result of the following formula:

$$b_i - (m'_i \otimes m_j) * \sigma(b_j)/\alpha$$

wherein:
$b_i = m'_i \otimes s$ is the correlogram associated to sample i,
$\alpha$ is a scaling coefficient,
s is a portion of duration T of the signal recorded by the detector,
$\sigma(b_j)$ is a filtered version of the chromatogram corresponding to sample j,
$m'_i$ is the derived correlation function associated to the injection timing sequence $m_i$,
$m_j$ is the timing injection sequence of sample j,
$\otimes$ is a circular correlation operator, and
$*$ is a circular convolution operator.

23. The method of claim 21, wherein $\alpha$ is (M+1)/2.

24. The method of claim 21, wherein the computing step is repeated multiple times, each time resulting in a better approximation of the individual chromatograms.

25. The chromatography device of claim 24, wherein the chromatography column is a gas chromatography column.

26. The chromatography device of claim 24, wherein the chromatography column is a liquid chromatography column.

27. The method of claim 1, wherein the step of analyzing data of interest is performed in real time, using the data from a moving time window having a duration at least equal to a duration of the longest of the specific injection timing sequences.

28. A chromatography device for analyzing at least two samples simultaneously, the chromatography device comprising:
a manifold comprising a plurality of inlets for injecting fractions of samples and an outlet,
a plurality of injectors, each injector being arranged at a corresponding inlet for selectively injecting a fraction of fluid sample from said inlet,
a control unit configured for controlling the state of each injector according to a specific injection timing sequence derived from a pseudo-random binary sequence,
a chromatography column connected at the outlet of the manifold,
a detector placed at the outlet of the chromatography column and configured to acquire a signal for a period of time at least equal to a duration of a longest of said specific injection timing sequences; and
a signal processing unit configured to:
cross-correlating the signal acquired by the detector and a derived correlation function, said derived correlation function being derived from the pseudo-random binary sequence associated with said sample, so as to obtain an individual correlogram signal specific to the sample; and
analyzing data of interest of the individual correlogram signal so as to obtain an independent output signal indicative of the composition of the sample.

* * * * *